United States Patent [19]

Cassidy et al.

[11] Patent Number: 5,567,359
[45] Date of Patent: *Oct. 22, 1996

[54] ULTRA MILD SURFACTANT WITH GOOD LATHER

[75] Inventors: William A. Cassidy, Norwood; James R. Schwartz; Richard D. Farris, both of West Chester, all of Ohio

[73] Assignee: The Proctor & Gamble Company, Cincinnati, Ohio

[*] Notice: The term of this patent shall not extend beyond the expiration date of Pat. No. 5,084,212.

[21] Appl. No.: 460,025

[22] Filed: Jun. 2, 1995

Related U.S. Application Data

[63] Continuation of Ser. No. 799,916, Nov. 26, 1991, abandoned, which is a continuation of Ser. No. 459,100, Dec. 29, 1989, abandoned.

[51] Int. Cl.$^6$ .......................... C11D 1/755; C11D 10/04
[52] U.S. Cl. ............................ 510/135; 510/141
[58] Field of Search .................... 252/554, 546, 252/548, 547, 174.17, 174, DIG. 5, 117, 121, 132, 134, 174.23, 174.24, 108, 535, 549; 562/110

[56] References Cited

U.S. PATENT DOCUMENTS

| | | | |
|---|---|---|---|
| 2,988,511 | 6/1961 | Mills et al. | 252/121 |
| 2,989,547 | 6/1961 | Whyte | 260/348 |
| 3,024,273 | 3/1962 | Whyte et al. | 260/513 |
| 3,824,102 | 7/1974 | Ishihara et al. | 430/545 |
| 4,180,470 | 12/1979 | Tokosh et al. | 252/121 |
| 4,673,525 | 6/1987 | Small et al. | 252/132 |
| 5,084,212 | 1/1992 | Farris et al. | 252/554 |
| 5,322,643 | 6/1994 | Schwartz et al. | 252/554 |

OTHER PUBLICATIONS

T. J. Franz, J. Invest. Dermatol., 1975, 64, pp. 190–195 (month unknown).

*Primary Examiner*—Prince Willis, Jr.
*Assistant Examiner*—Alan D. Diamond
*Attorney, Agent, or Firm*—Tara M. Rosnell; D. K. Dabbiere

[57] ABSTRACT

This invention comprises a synthetic surfactant composition which provides ultra skin mildness, and excellent lather. This invention is based on an ultra mild surfactant composition comprising: $C_8$ alkyl glyceryl ether sulfonate $C_8$ (AGS). The $C_8$ AGS offers a remarkable combination of desirable properties for mild cleansing formulations.

6 Claims, 3 Drawing Sheets

5,567,359

ULTRA MILD SURFACTANT WITH GOOD LATHER

This is a continuation of application Ser. No. 07/799,916, filed on Nov. 26, 1991 now abandoned; which is a continuation of application Ser. No. 07/459,100, filed Dec. 29, 1989, now abandoned.

TECHNICAL FIELD

This invention relates to mild surfactants with good lather.

BACKGROUND OF THE INVENTION

This invention relates to mild surfactants and to cleansers comprising mild synthetic surfactants.

Personal cleansing with mild surface-active cleansing preparations has become a focus of great interest. Many people wash and scrub their skin and hair with various surface-active preparations frequently. Ideal cleansers should cleanse gently, causing little or no irritation, without defatting and overdrying after frequent routine use. Most lathering soaps, shampoos, dishwashing liquids, etc., fall short in this respect.

Mild Surfactants

For background on the uses and preparation of mild alkyl glyceryl ether sulfonates see Hulter U.S. Pat. Nos. 2,094,489, issued Sep. 28, 1937; Smith 2,427,576, issued Sep. 16, 1947; Smith 2,427,577, issued Sep. 16, 1947; and Mills et al. 2,988,511, issued Jun. 13, 1961, all incorporated herein by reference. See also Whyte U.S. Pat. Nos. 2,989,547, issued Jun. 20, 1961; Pilcher et al. 2,999,068, issued Sep. 5, 1961; and Whyte et al. 3,024,273, issued Mar. 6, 1962, all incorporated herein by reference. While the prior art discloses the preparation and/or the use of alkyl glyceryl ether sulfonate (AGS) per se (e.g., U.S. Pat. No. 3,024,273, supra), many do not even mention $C_8$ AGS, and none uses a $C_8$ AGS in a personal cleansing example.

Likewise, Tokosh et al. U.S. Pat. No. 4,180,470, issued Dec. 25, 1979, discloses a detergent bar with from 2–6% of sodium alkoxy hydroxy propane sulfonate (AGS) with alkyl chains of from 8 to 22 carbon atoms; but only $C_{10}$, $C_{14}$, and $C_{18}$ AGS are used in the Examples and only at levels of 4–5%. A small amount of sodium chloride is also required. The detergent bar is predominately acyl isethionate. The AGS and salt are used to improve bar wear rate without adversely affecting its lathering characteristics. No advantage of using $C_8$ AGS is suggested and it is not used in a working example.

In an unrelated art, Ishihara et al. U.S. Pat. No. 3,824,102, issued Jul. 16, 1974, discloses $C_8$ AGS in high speed silver iodobromide emulsion for photographic coating composition. No $C_8$ AGS purity details are disclosed.

A major drawback of most mild synthetic surfactant systems when formulated for skin or hair cleansing is poor lather performance. The use of high sudsing anionic surfactants can yield acceptable lather volume. Unfortunately, the highest sudsing anionic surfactants are, in fact, poor in skin "patch test" mildness. While the moderately mild sodium lauryl glyceryl ether sulfonate ($C_{12}$ AGS), is relatively good in lather potential, the ultra mild $C_{18}$ AGS is very poor in lather potential. It will be appreciated that mildness and lather, make surfactant selection a delicate balancing act. Thus, it will be appreciated that rather stringent requirements for mild cleansers limit the choice of surface-active agents and final formulations represent some degree of compromise. Mildness is often obtained at the expense of effective cleansing and lathering. Needless to say, an ultra mild surfactant with good lather potential is hard to find.

OBJECTS OF THE INVENTION

An object of the present invention is to provide an ultra mild surfactant with acceptable lather potential.

Other objects will become apparent from the detailed description below.

SUMMARY OF THE INVENTION

This invention is based on an ultra mild, good lathering, alkyl glyceryl ether sulfonate surfactant composition comprising at least about 65% $C_{7-9}$ alkyl glyceryl ether sulfonate ($C_8$ AGS) and no more than 35% of higher alkyl chained AGS.

DETAILED DESCRIPTION OF THE INVENTION

The invention relates to an ultra mild surfactant composition with surprisingly acceptable lather potential. The $C_8$ AGS offers a remarkable combination of desirable properties for mild cleansing formulations which have superior skin mildness and acceptable lather benefits. $C_8$ AGS can be used in shampoos, toilet bars, light duty liquids, or any other surfactant-based product which comes in contact with the skin.

Commonly assigned Small et al. U.S. Pat. Nos. 4,673,525, issued Jun. 16, 1987, and Stiros 4,338,211, issued Jul. 6, 1982, hereby incorporated herein by reference, disclose personal cleansing products in which the ultra mild AGS surfactant of this invention can be used for improvements of such already mild products.

The preferred cation in the AGS salt is sodium. However, other cations such as triethanolammonium (TEA), ammonium, and K, etc., are also usable.

The percentages, ratios, and parts herein are on a total composition or surfactant weight basis, unless otherwise specified. All levels and ranges herein are approximations unless otherwise specified.

The ultra mild $C_8$ AGS which has a Relative Skin Barrier Destruction Value (as defined hereinbelow) of less than about 1, and any one with a Value of 1 or greater is excluded. The Relative Skin Barrier Destruction Value is a mildness value based on Standard AGS.

Figure 2:
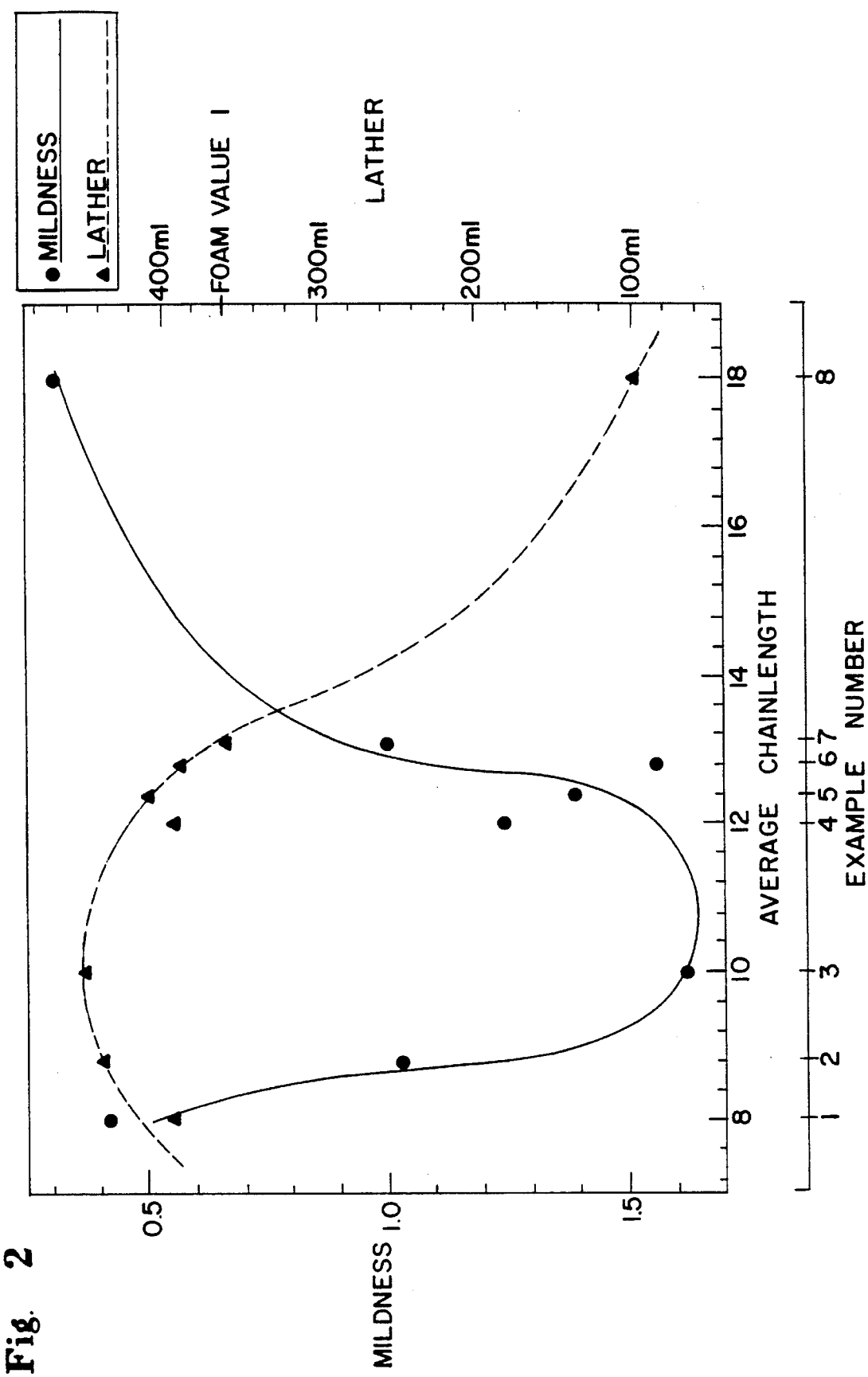
FIG. 2 shows comparative lather volume and mildness results of a $C_8$ AGS surfactant solution vs. various other AGS surfactant solutions.
Figure 3:
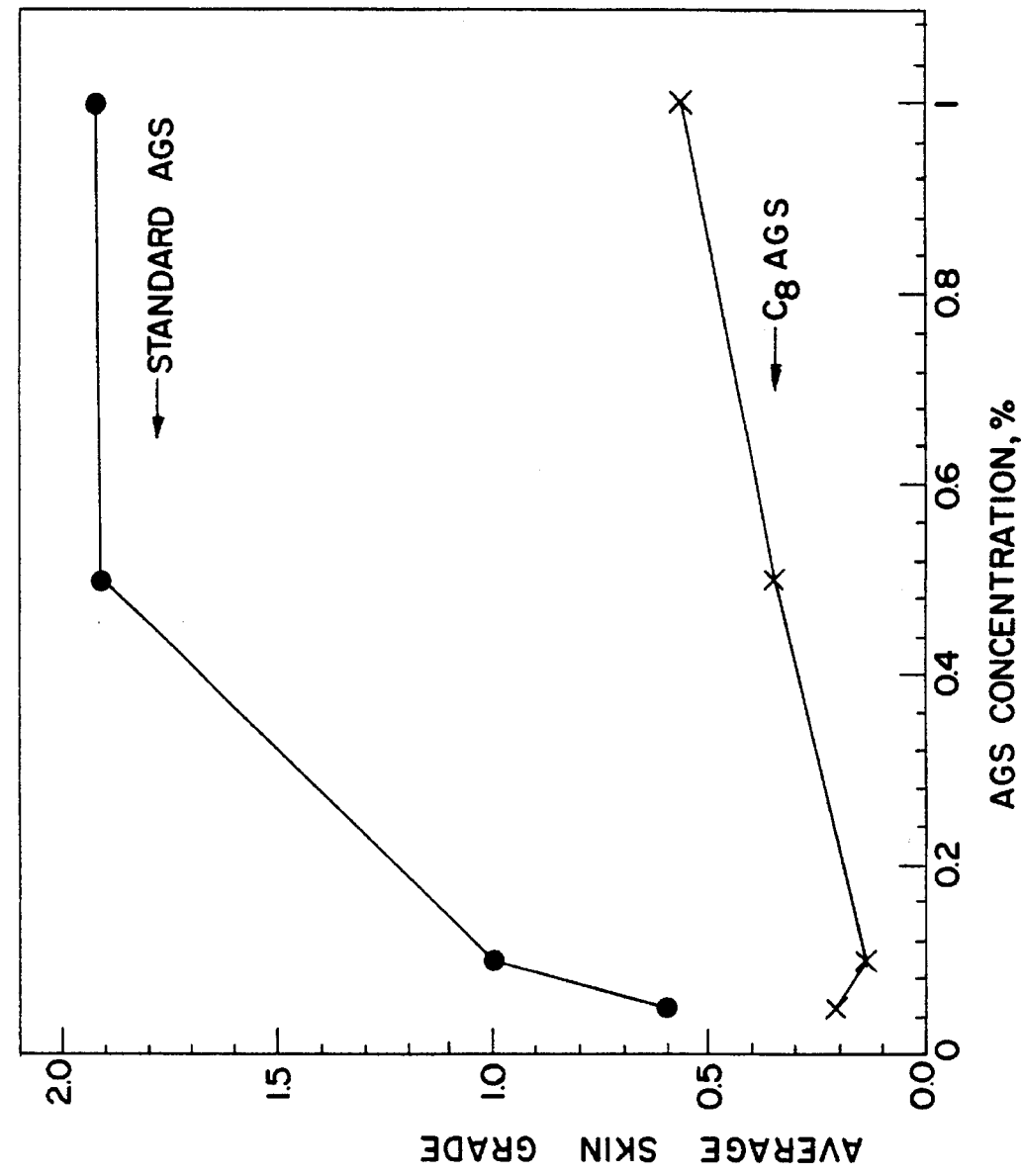
FIG. 3 shows mildness patch test results for various concentrations of $C_8$ AGS (Example 1) vs. a Standard (Example 7) mixture of AGS.

The Standard AGS surfactant has an alkyl carbon chain distribution of 58% $C_{12}$; 21% $C_{14}$; 10% $C_{16}$; and 9% $C_{18}$ (58/21/10/9 $C_{12}/C_{14}/C_{16}/C_{18}$). The Standard has a Relative Skin Barrier Destruction Value of 1 by definition. The ultra mild AGS surfactant of this invention preferably has a Relative Skin Barrier Destruction Value of less than about 0.9 and is preferably a better foamer than the prior art Standard, Example 7, as shown in FIGS. 2 and 3. The ultra mild surfactant of this invention comprises alkyl glyceryl ether sulfonate (AGS) which has from about 65% to about 100% of an AGS surfactant with an alkyl backbone chain of from about 7 to about 9 carbon atoms, or mixtures thereof. The alkyl has a total of no more than 10 carbon atoms. AGS is derived from a corresponding ether.

In other words, the present invention is an ultra mild, good foaming surfactant comprising alkyl glyceryl ether sulfonate (AGS) surfactant. The ultra mild AGS surfactant has a hydrophobic group which contains a linear alkyl chain containing from about 7 to 9 carbon atoms, and which can contain methyl or ethyl alkyl branch groups for a total of up to about 10 carbon atoms, e.g., those derived from ethyl octanol, methyl octanol, and the like.

A preferred ultra mild AGS surfactant of this invention contains no more than about 35%, preferably less than 30%, and more preferably less than 25%, of other AGS with linear alkyl chains of 10 or higher carbon atoms. A preferred ultra mild AGS of this invention has from about 75% to about 90% $C_8$ alkyl chains. A more preferred ultra mild AGS surfactant of this invention has at least about 80% AGS surfactant having alkyl chains of from 7 to 9 straight chain carbon atoms, methyl or ethyl branch chains up to about 10 carbon atoms, and mixtures thereof. The preferred ultra mild AGS surfactant comprises a hydrophobic linear chain containing about 100% eight carbon atoms and has a Relative Skin Barrier Destruction Value of from about 0 to about 0.9, more preferably from about 0.1 to about 0.5.

In Vitro Skin Barrier Destruction Test

The skin barrier destruction test (see test apparatus in FIG. 1) is used to assess the irritancy potential of surfactants. In this test the milder the surfactant, the lesser the skin barrier 4 is destroyed. Skin barrier destruction is measured by the relative amount of radio-labeled water ($^3H$—$H_2O$) which passes from the test solution 3 through the skin epidermis 5 into the physiological buffer contained in the diffusate chamber 6. (This test is also described by T. J. Franz in the *J. Invest. Dermatol.*, 1975, 64, pp. 190–195.)

Figure 1:
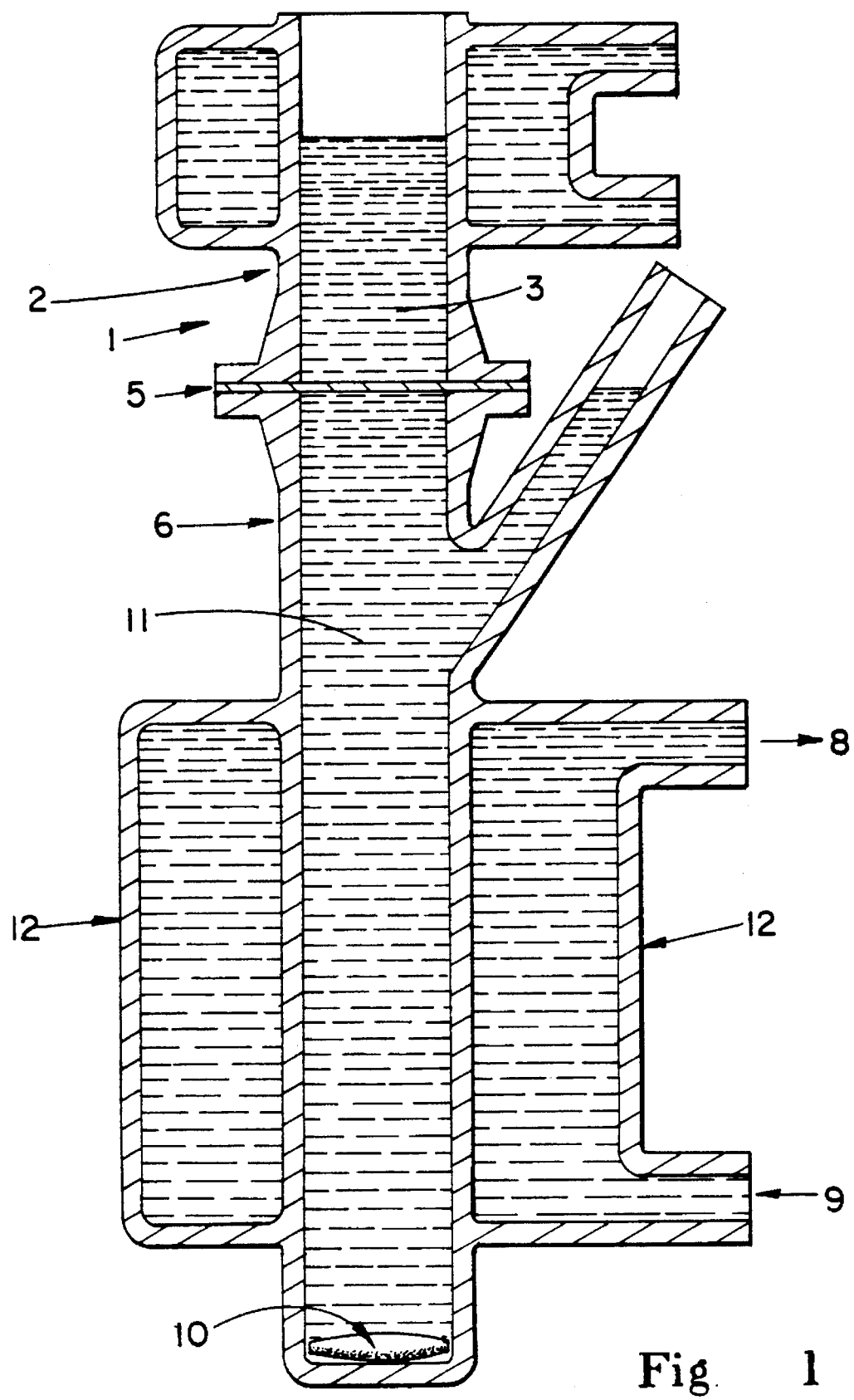
FIG. 1 shows a static diffusion cell diagram which is used to measure surfactant mildness.

The skin barrier destruction test utilizes a static diffusion cell 1 diagrammed in FIG. 1. Human skin epidermis 5 is placed on the flat area of the diffusate chamber 6 which is filled with physiological buffer (pH 7.4) 11 for collection of the transported radio-labeled water. The diffusate chamber 6 is either surrounded by a water jacket 12 or placed in an aluminum heating block for temperature control. Temperature can thus be provided by circulating water (outflow 8 and inflow 9) pumped from a water bath at a predetermined temperature. A water-jacketed top is connected to a second circulator/temperature bath. Both the diffusate chamber 6 and the test solution reservoir 2 are maintained at 37° C. An O-ring joint clamp secures the test solution reservoir 2, sandwiching the skin epidermis 5 in between it and the diffusate chamber 6.

This test uses cells which have a diffusion area of 0.20 $cm^2$. The diffusate chamber 6 holds approximately 5 ml. The bottom of the chamber 6 is flattened to allow spinning of a small magnetic stirring bar 10. The bars 10 are spun by a series of permanent magnets attached to individual electric motors.

The test solution reservoir 2 holds approximately 1 ml of test solution 3. During testing the tops of reservoir 2 are sealed with Parafilm to inhibit evaporation and prevent spillage.

Human abdominal skin is obtained from a local skin bank which procured and processed the skin for protective freezing and storage as described by V. P. Perrin (J. Cryosurgery, 1968, 1, 89–99). The sheets of skin are supplied as 0.012" thickness pieces shipped and maintained on dry ice until used. The skin is then thawed by submerging individual packets under warm (–95° F.) running water for 3–5 minutes. The skin is then cut into ¾"×¾" squares for mounting onto the diffusion cells.

Test Procedure

The following discussion describes the In Vitro Skin Barrier Destruction Test procedure. Use either 55 or 25 cells per test, 5 replicates per treatment. This permits testing of either 10 or 4 surfactant solutions plus a water control. Due to the large variability in percutaneous transport (site to site and individual to individual), the water control is a mandatory reference point for each experiment.

Dose test solutions are prepared on a weight/weight basis at 0.5% on a top-loading (±0.01 g) balance. Since each static diffusion cell 1 is dosed with 0.50 ml, a minimum of 3 ml of each test solution 3 should be prepared (5 doses+standard). Each solution is spiked with $^3H$—$H_2O$ to an approximate activity of 1.8 milliCurie/ml dosing solution. This insures a sufficient level of $^3H$ transport for the sampling interval.

During sample collection, the entire volume of the diffusate chamber 6 is emptied through the sampling port 7, rinsed, and refilled with fresh buffer solution 11. Samples are collected at 3, 6, and 24 hours after initial dosing. The sample plus rinse is emptied into a scintillation vial and analyzed by liquid scintillation counting.

Standards are included for each sample. One hundred and 200 microliter samples are placed in individual scintillation vials and brought to 7 ml total volume with buffer solution. The counts per minute (cpm) for diffusate samples are converted to equivalent mg water.

All data represent the total quantity of $^3H$—$H_2O$ which penetrate the skin during a 24 hour test duration. Relative Skin Barrier Destruction Values (relative mildness) are calculated for the AGS surfactants of Examples 1–8 described below in Tables 1 and 2 and illustrated in FIG. 2. This is done by dividing the mg of water penetrated for each Example by that penetrated for the Standard AGS mixture of Example 7. Thus, numbers greater than 1 indicate greater skin irritation potential than the Standard AGS mixture of Example 7. On the other hand, numbers less than 1 represent AGS surfactants milder than the Standard.

Relative Foam Volume Potential

In addition to improved and unexpected mildness, the foam volume potential of the $C_8$ AGS is important. Thus, a Relative Foam Volume Potential Test is devised to show $C_8$ AGS's unexpected good foam volume potential. In short, the Relative Foam Volume Potential of the $C_8$ AGS surfactants of the present invention is at least about 75% as good or better than the Standard AGS. A quantitative blender foam (lather potential) volume test is used to measure the Relative Foam Volume Potential of surfactants.

Equipment

1. Specially designed 500 ml graduate cylinder adapted with blender impeller. The sharp edge of the impeller blade (2.3 cm) is the trailing edge.

2. Waring Blender Base No. 7011-31BL92 with high/low speed switch.
3. Variac Voltage Regulator. Voltage to blender is adjusted so that blender disk rotates at 18,000 rpm unloaded (with no cylinder on).

Procedure

1. A 0.5% Solution (dry weight) of the surfactant in tap water is used.
2. Warm and clean cylinder by rinsing it with hot tap water. Drain water from cylinder and check to make sure solution temperature is 95°–105° F. (about 37° C.). (If solution is too cool, it can be warmed gently on a hot plate. Cylinder should be rinsed again if it becomes cool while this is being done.)
3. Pour 82 ml of solution into cylinder; put cylinder on blender base. Turn blender on for ten seconds, after checking to make sure Variac is set on line.
4. Wait ten seconds and record level of the top of the layer of foam.
5. Repeat procedure with a new solution.

The Relative Foam Volume Potential of the Standard AGS is given the value of "1". The $C_8$ AGS and several other AGS surfactant mixtures and their Relative Foam Volume Potential values are shown in FIG. 2 and below in Tables 1 amd 2. The $C_8$ AGS has a Relative Foam Volume Potential Value of at least 0.75, and preferably from about 1 to about 1.15.

Cleansing Compositions Containing $C_8$ AGS

In summary, a number of cleansing products can be formulated using the ultra mild $C_8$ AGS as a major or primary surfactant. Small et al. U.S. Pat. Nos. 4,673,525, issued Jun. 16, 1987; and 4,812,253, issued Mar. 14, 1989; and Stiros 4,338,211, issued Jul. 6, 1982; all hereby incorporated herein by reference, disclose several personal cleansing products. The present $C_8$ AGS invention can be employed as the sole, a primary, or co-surfactant, along with one or more ingredients selected from polymeric skin feel aids, moisturizers, fillers, soaps, etc., to provide improved mildness of the prior art product. The following patents disclose or refer to such ingredients and formulations, and are hereby incorporated herein by reference:

| Pat. No. | Issue Date | Inventor(s) |
| --- | --- | --- |
| 3,761,418 | 9/1973 | Parran, Jr. |
| 4,234,464 | 11/1980 | Morshauser |
| 4,061,602 | 12/1977 | Oberstar et al. |
| 4,472,297 | 9/1984 | Bolich et al. |
| 4,491,539 | 1/1985 | Hoskins et al. |
| 4,540,507 | 9/1985 | Grollier |
| 4,673,525 | 6/1987 | Small et al. |
| 4,704,224 | 11/1987 | Saud |
| 4,812,253 | 3/1989 | Small et al. |
| 4,820,447 | 4/1989 | Medcalf et al. |

A preferred shampoo composition comprises 1–25%, preferably 3–15%, mild $C_8$ AGS, 2–25% total foam enhancer and balance water or liquid. A preferred liquid facial cleanser comprises 1–25%, preferably 5–15%, $C_8$ AGS. A preferred dishwashing liquid comprises from about 3% to about 25% mild $C_8$ AGS, preferably from about 5% to about 20%, and more preferably from about 10% to about 15% of the ultra mild $C_8$ AGS. In contrast, liquids made with the Standard AGS alone have a phase separation problem at levels of AGS of over about 0.5%, and with a good co-surfactant the Standard AGS has a phase separation problem at levels of over about 4–5% by weight of the aqueous liquid. $C_8$ AGS, on the other hand, can be used at levels up to about 20%, preferably at levels of about 5–18%, by weight of the liquid.

A preferred ultra mild skin cleansing composition is a toilet bar comprising: from 10–80%, preferably from 20–50%, mild $C_8$ AGS surfactant; from 10–40% moisturizer; from 0.1–5% polymeric skin feel aid, and from 5–25% soap. The synthetic surfactant and soap preferably have a ratio of from 2:1 to 12:1, more preferably the synthetic to soap ratio is from 4:1 to 10:1, or from 6:1 to 9:1.

In this respect, limited amounts of other surfactants can be used with the ultra mild $C_8$ AGS surfactant of this invention. Numerous examples of other surfactants are disclosed in the above incorporated by reference patents. They include alkyl sulfates, soaps, other suitable alkyl glyceryl ether sulfonates (AGS), anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these surfactants are $C_{10}$–$C_{22}$, preferably $C_{10}$–$C_{18}$. Alkyl glycosides and methyl glucose esters are preferred mild nonionics which may be mixed with at least one of said mild anionic or amphoteric surfactants in the compositions of this invention. Soaps at levels of 1–25%, preferably 5.5–15%, can be included, particularly in bar compositions. The soaps are preferably made in situ via adding a base, e.g., NaOH, to convert free fatty acids in the composition mix.

The other ingredients can be used for the various applications. E.g., perfumes can be used in formulating the skin cleansing products, generally at a level of from about 0.1% to about 1.5% of the composition. Alcohols, hydrotropes, colorants, and fillers such as talc and clay, can also be used. Preservatives, e.g., sodium ethylenediaminetetraacetate (EDTA), generally at a level of less than 1% of the composition, can be incorporated in the cleansing products to prevent microbiological growth. Antibacterials can also be incorporated, Usually at levels up to 1.5%.

Foam Enhancers

The ultra mild surfactant, sodium $C_8$ glyceryl ether sulfonate, as defined herein, is ultra mild and is an acceptable foamer. This is demonstrated in in vitro non-clinical mildness testing and foam potential reports (FIG. 2). While desirable to incorporate into a skin cleanser for its mildness properties, this $C_8$ AGS alone may not provide optimum lather creaminess for certain executions; thus, foam enhancers can be added to provide optimum lather creaminess, volume, and/or stability.

The percentage of foam enhancer is defined herein as the Relative Amount by weight of Foam Enhancer to total surfactant unless otherwise specified. For example, a typical liquid shampoo has about 17% total surfactant (e.g., 13% $C_8$ AGS plus 4% $C_{12}$–$C_{13}$ alkyl polyglycoside). Here the foam enhancer level is 4% and the total surfactant level is 17%, so the relative level of the foam enhancer is 4/17 or 23.5% of the total surfactant. With the exception of certain salts, the foam enhancers are considered part of the total surfactant, for purposes of this calculation.

Alkyl polyglycoside detergents are good $C_8$ AGS foam enhancers. The alkyl group can vary from about 8 to about 22 and the glycoside units per molecule can vary from about 1.1 to about 5 to provide an appropriate balance between the hydrophilic and hydrophobic portions of the molecule. Combinations of $C_8$–$C_{18}$, preferably $C_{12}$–$C_{16}$, alkyl polyglycosides with average degrees of glycosidation ranging from about 1.1 to about 2.7, preferably from about 1.2 to about 2.5, are preferred. These types can be used at a relative level based on the total surfactant of from about 5% to about 60%, preferably from about 20% to about 50%, and, in some products, from about 22% to about 35% is preferred.

Amine oxide detergents are good $C_8$ AGS foam enhancers. Some preferred amine oxides are $C_8$–$C_{18}$, preferably $C_{10}$–$C_{16}$, alkyl dimethyl amine oxides and $C_8$–$C_{18}$, preferably $C_{12}$–$C_{16}$, fatty acyl amidopropyl dimethyl amine oxides and mixtures thereof. These types of foam enhancers can be used at a relative level of from about 5% to about 30%, preferably from about 8% to about 20% of the total surfactant.

Fatty acid alkanolamides are good $C_8$ AGS foam enhancers. Some preferred al kanol amides are $C_8$–$C_{18}$, preferably $C_{12}$–$C_{16}$, monoethanolamides, diethanolamides, and monoisopropanolamides and mixtures thereof. These types of foam enhancers can be used at a relative level of from about 10% to about 30%, preferably from about 12% to about 20% of the total surfactant.

Betaines are good foam enhancers. Betaines such as $C_8$–$C_{18}$, preferably $C_{12}$–$C_{16}$, alkyl betaines, e.g., coco betaines or $C_8$–$C_{18}$, preferably $C_{12}$–$C_{16}$, acyl amido betaines, e.g., cocoamidopropyl betaine, and mixtures thereof, are preferred. These are used at a relative level of from about 10% to about 30%, preferably from about 12% to about 20% of the total surfactant.

Water-soluble halide salts can be used as $C_8$ AGS foam enhancers. Sodium, magnesium, potassium, ammonium, monoethanolamine, diethanolamine, and triethanolamine (TEA) chloride salts are preferred. These types can be used at a relative level of from about 10% to about 30%, preferably from about 12% to about 20% of the total surfactant. $MgCl_2$ is the preferred salt.

$C_8$ AGS "acetone solubles" can be used as foam enhancers. These types of foam enhancers are described in more detail herein and can be used at a relative level of from about 10% to about 40%, preferably from about 15% to about 30%. The principal components of the acetone solubles are propane-1,2-diol alkyl ether and diglyceryl alkyl ether described hereinbelow. The alkyl groups correspond to the starting materials.

Certain other surfactants can be used in combination with $C_8$ AGS to provide a creamier and more stable lather. One such surfactant is sodium lauroyl sarcosinate (trade name Hamposyl L, made by Hampshire Chemical).

EXAMPLES

The following examples and methods are illustrative and are not intended to limit the scope of the invention(s). More details and alternative methods of making and purifying generic alkyl glyceryl ether sulfonate are disclosed in Mills and Korsi U.S. Pat. No. 2,988,511, issued Jun. 13, 1961, incorporated herein by reference. All levels and ranges, temperatures, results etc., used herein are approximations unless otherwise specified. The following AGS Examples are all made with saturated straight chain alcohols.

Example 1

Step 1 is the production of alkyl chloroglyceryl ether. One thousand grams of octanol ($C_8$ alcohol) are charged to a reaction flask and heated to 150° F. (65° C.). About 4 ml of stannic chloride are added, avoiding exposure to the air outside the reaction flask. (About 2–8 ml of stannic chloride can be added.) The reaction mix is well stirred and maintained at a temperature of 145°–150° F. (60°–65° C.) while 800 grams of epichlorohydrin are slowly added at a rate of about one drop per minute. After all the epichlorohydrin has been added the mixture is maintained at a temperature of 150° F. (65° C.) for 90 minutes more.

Step 2 is the production of alkyl glycidyl ether. Three hundred grams of alkyl chloroglyceryl ether of Step 1, 183 grams of water and 69 grams of sodium hydroxide are charged to a well stirred flask and heated to 190° F. (84° C.) for one hour. Stirring is stopped and the mixture allowed to cool to room temperature. The organic layer is separated from the aqueous layer.

Step 3 is sulfonation using as starting reagents 74 grams of alkyl glycidyl ether of Step 2, 90 grams of water, 36 grams of sodium meta-bisulfite and 3 grams of sodium hydroxide are charged to an autoclave. If available. A heel of $C_8$ AGS from earlier production, about 10% of the total reaction mass, is added to the starting reagents. Sodium ethylenediaminetetraacetate (EDTA) is added as a processing aid to chelate metals such as iron. The mixture is well stirred and heated until it reaches a temperature of about 360° F. (182° C.) (exothermic heat of reaction will supply part of the heating). The reaction mix is held at 360° F. (182° C.) for about 25 minutes and then cooled to room temperature. The pH is adjusted to about 9 with sodium hydroxide. This product is 100% $C_8$ AGS discounting non-AGS materials. It is identified as Example 1 in Table 1. See U.S. Pat. No. 2,988,511, supra, for detailed alternative methods of making and purifying AGS.

Comparative Example 2

Step 1. The production of a 60/40 $C_8$–$C_{10}$ alkyl chloroglyceryl ether is the-same as in Example 1, except that 352 grams of $C_8$–$C_{10}$ alcohol and 262 grams of epichlorohydrin are used. (The alcohol is about 3 parts octanol to about 2 parts decanol.)

Step 2. The production of alkyl glycidyl ether is the same as in Example 1, except that 622 grams of alkyl chloroglycerol ether, 148 grams of sodium hydroxide and 417 grams of water are used.

Step 3. The sulfonation is the same as in Example 1, except that 57.6 grams of alkyl glycidyl ether, 59 grams of water, 24.5 grams of sodium meta-bisulfite, and 2.4 grams of sodium hydroxide are used. This product is about 60/40 $C_8$/$C_{10}$ AGS as reported in Table 1. Note that the mildness value reported in Table 2 is about 1. A 65/35 $C_8$/$C_{10}$ AGS has a mildness value of less than 1. See the mildness curve in FIG. 2.

Comparative Example 3

Step 1. The production of a $C_{10}$ alkyl chloroglyceryl ether is the same as in Example 1, except that 283 grams of decyl alcohol and 187 grams of epichlorohydrin are used.

Step 2. The production of alkyl glycidyl ether is the same as in Example 2.

Step 3. The sulfonation is the same as in Example 1, except that 300 grams of alkyl glycidyl ether, 390 grams of water, 108 grams of sodium meta-bisulfite, and 11 grams of sodium hydroxide are used. This product is about 100% $C_{10}$ AGS.

Comparative Example 4

Step 1. The production of a $C_{12}$ alkyl chloroglyceryl ether is the same as in Example 1, except that 345 grams of dodecyl alcohol and 193 grams of epichlorohydrin are used.

Step 2. The production of alkyl glycidyl ether is the same as in Example 2.

Step 3. Sulfonation is the same as in Example 1, except that 80 grams of alkyl glycidyl ether, 94 grams of water, 24.8 grams of sodium meta-bisulfite, and 2.5 grams of sodium hydroxide are used. This product is about 100% $C_{12}$ AGS.

Comparative Example 5

A 65/26/6 $C_{12}/C_{14}/C_{16}$ alkyl glycidyl ether is obtained from a Procter & Gamble commercial production. The sulfonation step is the same as in Example 1, except that 36.6 grams of alkyl glycidyl ether, 42.4 grams of water, 11 grams of sodium meta-bisulfite, and 1.17 grams of sodium hydroxide are used. A 65/$C_{12}$, 26/$C_{14}$ and 6/$C_{14}$ AGS mixture is the product.

Comparative Examples 6 and 7

The AGS of Example 6 and the AGS Standard Example 7 are commercial cuts obtained from Procter & Gamble. Their alkyl chain distributions are, respectively, 68/25/7 $C_{12}/C_{14}/C_{16}$ and the Standard 58/21/10/9 $C_{12}/C_{14}/C_{16}/C_{18}$ as reported in Tables 1 and 2.

Comparative Example 8

Step 1. The production of the $C_{18}$ alkyl chloroglyceryl ether is the same as in Example 1, except that 396 grams of octadecyl alcohol and 260 grams of epichlorohydrin are used.

Step 2. The production of alkyl glycidyl ether is the same as in Example 1, except that 660 grams of $C_{18}$ alkyl chloroglyceryl ether, 232 grams of sodium hydroxide and 926 grams of water are used.

Step 3. The sulfonation is the same as in Example 1, except that 107 grams of $C_{18}$ alkyl glycidyl ether, 134 grams of water, 36.4 grams of sodium meta-bisulfite, and 3.2 grams of sodium hydroxide are used.

In general, after Step 3, any remaining water phase is separated from the AGS surfactant paste. If completion is not good, the paste can be purified by washing with warm ethyl acetate and/or ethanol.

TABLE 1

Summary of Surfactant Chain Lengths Used in Examples 1–8

| Example | AGS Alkyl Chain Length Distribution | | | | | | Average Chain Length |
|---|---|---|---|---|---|---|---|
| | $C_8$ | $C_{10}$ | $C_{12}$ | $C_{14}$ | $C_{16}$ | $C_{18}$ | |
| 1 | 100 | — | — | — | — | — | 8.0 |
| 2 | 60 | 40 | — | — | — | — | 8.8 |
| 3 | — | 100 | — | — | — | — | 10.0 |
| 4 | — | — | 100 | — | — | — | 12.0 |
| 5 | — | — | 65 | 26 | 6 | — | 12.4 |
| 6 | — | — | 68 | 25 | 7 | — | 12.8 |
| 7 | — | — | 58 | 21 | 10 | 9 | 13.1 |
| 8 | — | — | — | — | — | 100 | 18.0 |

Table 1 sets out the AGS compositions of Examples 1–8. Their Relative Foam Volumes and Mildness Values are reported in Table 2 and are shown in FIG. 2. All Examples except Example 1 comprise more than 35% $C_{10}$–$C_{18}$ AGS. Note that the AGS surfactants of Comparative Examples 2–6 are harsher than the Standard AGS Example 7. But the $C_8$ AGS, Example 1, is milder, showing a Relative Skin Barrier Destruction Value is only 0.42. Its Relative Foam Volume Potential Value is 1.10, which is much better than the Standard "1". However, a Relative Foam Volume Potential of about 0.75 or 0.85 is acceptable so long as the $C_8$ AGS has a significant mildness advantage over the Standard.

TABLE 2

Foam Volumes and Mildness Values for Examples 1–8

| Example | Avg. Chain Length | Foam Volume (ml) (X/360) | Mildness* |
|---|---|---|---|
| 1 | 8.0 | 395** (1.10) | 0.42*** |
| 2 | 8.8 | 440 (1.22) | 1.03 |
| 3 | 10.0 | 450 (1.25) | 1.62 |
| 4 | 12.0 | 395 (1.10) | 1.24 |
| 5 | 12.4 | 410 (1.14) | 1.39 |
| 6 | 12.8 | 390 (1.08) | 1.56 |
| 7 | 13.1 | 360 (1.00)**** | 1.00**** |
| 8 | 18.0 | 100 (0.28) | 0.31 |

*Relative Skin Barrier Destruction Value.
**Average of two tests on one sample.
***Average of three tests on two samples.
****Reference Point "1" for mildness as well as for Relative Foam Volume Potential.

Foam Enhancer-Cylinder Test and Examples 9–15

In some executions, the enhancement of the foam potential of the $C_8$ AGS surfactant is desirable. The foam enhancement potential of a potential enhancer is measured by the Foam Enhancer-Cylinder Test as follows. Ten grams of surfactant solution (with and without foam enhancer) are added to 108 ml of 100° F. water of the desired hardness. To this is added 2 grams of artificial sebum. The mixture is stirred with a magnetic stirrer for 15 seconds at high speed, with care being taken not to generate a foam. The pH is adjusted to 6.5 using $NH_4OH$ or HCl, as appropriate. The resulting mixed solution is gently added to a 1000 ml graduated cylinder and stoppered. The cylinder is then mounted on a rotating device where it is rotated end-over-end for 20 complete revolutions in approximately 40 seconds. The foam volume in the cylinder is then read immediately, at 1 minute and at 2 minutes. Results are recorded as is, hence a reading of about 120 ml is indicative of no foam. In general, triplicate runs are made. In addition, the rotating apparatus is set up to handle 2 cylinders at a time.

TABLE 3

Artificial Sebum Composition

| Ingredient | Wt. % |
|---|---|
| Oleic Acid | 19.1 |
| Olive Oil | 21.57 |
| Palmitic Acid | 5.0 |
| Coconut Oil | 19.10 |
| Stearic Acid | 2.5 |
| Squalene | 6.0 |
| Paraffin Oil (light) | 5.0 |
| Cholesterol | 2.5 |
| Lanolin | 7.5 |
| Coconut Fatty Acid | 5.8 |
| Dodecane | 5.8 |
| Choleth-24 | 0.03 |

Examples 9–15

Examples 9–15, save Example 9, are prepared by adding the foam enhancers to base $C_8$ AGS at the levels shown in Table 4. The Relative Amount of Foam Enhancer for Example 9 is 0; for Example 10, 21%; for Example 11, 23%; for Example 12, 11%; for Example 13, 15%; and for Example 14, 18%; and for Example 15, 15%. Note that the 2-minute foam volume stability is improved for all foam enhancers. The levels of $C_8$ AGS and foam enhancers shown in Table 4 are on a dry weight basis.

TABLE 4

Foam Enhancement Data

| | Examples | | | | | | |
|---|---|---|---|---|---|---|---|
| Ingredients | 9 | 10 | 11 | 12 | 13 | 14 | 15 |
| $C_8$ AGS (100%) | 17 | 14 | 13 | 17 | 17 | 17 | 17 |
| Acetone Solubles | — | 3 | — | — | — | — | — |
| $C_{12-14}$ $G_{1.4}$ Alkyl Polyglycosides | — | — | 4 | — | — | — | — |
| Dimethyldodecyl-amine Oxide | — | — | — | 2 | — | — | — |
| Coco-Diethanol-amide | — | — | — | — | 3 | — | — |
| $MgCl_2$ | — | — | — | — | — | 3 | — |
| Cocoamidopropyl Betaine | — | — | — | — | — | — | 3 |
| Water | qs | qs | qs | qs | qs | qs | qs |
| Relative % Foam Enhancer | 0 | 18 | 24 | 11 | 15 | 18 | 15 |
| Cylinder Results: | | | | | | | |
| Initial Foam Volume (ml) | 445 | 400 | 515 | 360 | 450 | 500 | 540 |
| 2 Min. Foam Volume | 145 | 390 | 500 | 355 | 440 | 485 | 525 |

In the Foam Enhancer-Cylinder Test, 10 grams of the solutions are used. While the total surfactant levels in Examples 10–15 range from 17% to 20%, they all show improved foam stability or improved foam volume vs. Example 9. In Example 14, the $MgCl_2$ is not included as a surfactant, so its total surfactant level is 17%. Examples 9, 10, and 11 each have a total of 17% surfactant. Example 12 has a total of 19% surfactant. Examples 13 and 15 each have a total surfactant level of 20%. Examples 12, 13 and 15 maintain their foam stability when their total surfactant levels are lowered to 17%.

The Acetone Solubles of Example 10 are obtained by stirring about 100 grams of $C_8$ AGS product (43% moisture) with 500 ml of acetone at room temperature (23° C.) for about one hour. The resulting insoluble crystals are then filtered off using Whatman filter paper No. 1 on a Buchner funnel. The filtrate containing the acetone solubles is then concentrated on a Rotovap at about 45° C., with care being taken to avoid foaming. 50 ml of ethanol is then added and evaporated in order to form an azeotrope and distill off the water. Finally, about 150 ml of acetone is added to the resulting evaporated product. The resulting second crystallization crystals are gravity filtered. The second filtrate is then evaporated using the Rotovap. Approximately 4 gm of a clear acetone soluble liquid is isolated. Acetone can be substituted by solvents of similar polarity. L. R. Snyder, J. Chromatogr., 92, 223 (1974).

The "acetone soluble" fraction consists of a number of different components. The predominant component is propane-1,2-diol octyl ether (Structure I). Other components include, but are not restricted to water, octyl alcohol, $C_8$ AGS, and diglyceryl octyl ether (Structure II).

Structure I:

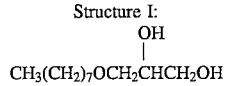

Structure II:

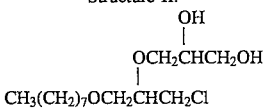

In Table 4, the "Cylinder Results" show that the acetone solubles are good foam enhancers. About 3 parts are added to about 14 parts $C_8$ AGS for improved foam volume stability, 390 ml vs. 145 ml of Example 9.

Example 16

In Table 5 is a light duty liquid made with 18% the $C_8$ AGS of Example 1. A comparable light duty liquid made with the Standard AGS of Example 7 has a serious stability problem at ordinary room temperatures. Phase separation is the problem for the light duty liquid made with a Standard AGS at an 18% level. Thus, the $C_8$ AGS light duty liquid of this Example provides a milder product, as well as a more stable product. ($C_8$ AGS can be used at levels of from about 5–20% by weight of such liquid products.)

TABLE 5

Light Duty Liquid

| Ingredient | Wt. % |
|---|---|
| Sodium $C_8$ AGS | 18 |
| Sodium $AE_{12}S$ | 8 |
| Dimethyldodecylamine oxide | 5 |
| Ethanol | 5 |
| Sodium cumene sulfonate | 2 |
| Sodium chloride | 2 |
| Miscellaneous (perfumes, colorants, etc.) | 3 |
| Water | 57 |
| Total | 100 |

The foam enhancer, dimethyldodecylamine oxide, is present at a relative foam enhancing level of about 16% by weight of the total surfactant system (5/31).

Examples 17–20

Toilet bars 17 and 18 of Table 6 are made using a procedure similar to that disclosed in U.S. Pat. No. 4,673, 525, supra, incorporated herein by reference.

TABLE 6

Examples of Bars Made with $C_8$ AGS

| Ingredient | Finished Bar (%) | |
| --- | --- | --- |
| | Example 17 | Example 18 |
| Sodium $C_8$ AGS | 67.25 | 52.25 |
| Stearic Acid | 0.90 | 0.90 |
| Coconut Fatty Acid | 8.10 | 8.10 |
| Sodium Soap (70/30 Tallow/Coconut) | 9.05 | 9.05 |
| Water | 4.00 | 4.00 |
| Polymer JR-400 (Amerchol) | 0.75 | 0.75 |
| Sodium Isethionate (GAF) | 5.00 | 5.00 |
| $TiO_2$ | 0.25 | 0.25 |
| Sodium Chloride | 4.00 | 4.00 |
| Perfume | 0.50 | 0.50 |
| Mayoquest 1545 (EDTA) | 0.20 | 0.20 |
| Cottonseed Triglyceride | — | 15.00 |
| Totals | 100.00 | 100.00 |

Toilet bars Examples 17 and 18 have an unexpected soap-like rinse feel attributed to the $C_8$ AGS.

Comparative toilet bars, Examples 19 and 20, are the same as the bars of Examples 17 and 18 except that the prior art Standard Example 7 AGS is used instead of the ultra mild $C_8$ AGS. These comparative bars, 19 and 20, are exemplary of the bars of U.S. Pat. No. 4,673,525, supra. Note that the AGS Patch Test data shown in FIG. 3 indicate that the $C_8$ AGS used in Bars 17 and 18 is significantly milder than the Standard AGS used in Bars 19 and 20. Likewise, the $C_8$ AGS used in Bars 17 and 18 is a better foamer than the Standard AGS used in Bars 19 and 20 as shown in Table 2 and FIG. 2.

Patch Test Protocol

The purpose of the patch test is to determine the level of primary skin irritation to human test subjects caused by three applications of a test AGS under conditions of occlusion.

Test Procedure: The subjects are 10 to 12 healthy adult volunteers between the ages of 18 and 65. Subjects are screened to eliminate those with pre-existing dermal allergies or active dermatitis.

The AGS are diluted with distilled water; dilutions are mixed thoroughly and may be heated slightly to aid in dissolution. Fresh dilutions are made prior to each patch application. Sufficient diluted test materials are applied to the patch to saturate the patch surface. Blenderm/Webril patches are used for this test.

Four patches are applied to the upper arms and reinforced with strips of a porous surgical tape of low irritation potential, e.g., MICROPORE® or SCANPOR®. The test is generally conducted according to the following schedule:

| | |
| --- | --- |
| Friday | First set of patches applied. |
| Saturday | Patches removed* by subject. |
| Monday | Patch sites visually assessed; grades assigned; second set of patches applied. |
| Tuesday | Patches removed* |
| Wednesday | Patch sites visually assessed; grades assigned; third set of patches applied. |
| Thursday | Patches removed* |
| Friday | Patch sites visually assessed; grades assigned. |

*After patch removal, test sites are rinsed using a moistened cloth or paper towel and patted dry.

Grading: The grading is done by an individual who is familiar with the evaluation of skin reactions and with the 0–4 grading scale (see Table 7). If a subject receives a grade two or higher on any test site at any grading session, that particular site is not re-patched, but the site is graded to the completion of the test. In these cases, a score of 2.0 or the actual grade (whichever is higher) is assigned as the final grade and is used for evaluating the data.

TABLE 7

Uniform Laboratory Patch Test Grading Scale

| | |
| --- | --- |
| 0 | No apparent cutaneous involvement. |
| ½ | Greater than 0, less than 1. |
| 1 | Faint but definite erythema, no eruptions or broken skin or no erythema but definite dryness; may have epidermal fissuring. |
| 1 ½ | Greater than 1, less than 2. Moderate erythema, may have a few papules or deep fissures, moderate-to-severe erythema in the cracks. |
| 2 ½ | Greater than 2, less than 3. Severe erythema (beet redness), may have generalized papules or moderate-to-severe erythema with slight edema (edges well defined by railing). |
| 3 ½ | Greater than 3, less than 4. Generalized vesicles or eschar formations or moderate-to-severe erythema and/or edema extending beyond the area of the patch. |
| Typical Examples of-Half-Grad Scores | |
| ½ | Faint, barely perceptible erythema or slight dryness (glazed appearance). |
| 1 ½ | Well-defined erythema or faint erythema with definite dryness, may have epidermal fissuring. |
| 2 ½ | Moderate erythema with barely perceptible edema or severe etythema not involving a significant portion of the patch (halo effect around the edges), may have a few papules or moderate-to-severe erythema. |
| 3 ½ | Moderate-to-severe erythema with moderate edema (confined to patch area) or moderate-to-severe erythema with isolated eschar formations or vesicles. |

Results: For each test material, the average of all scores (10–12 subjects, 3 grading sessions) is calculated and reported as the average skin grade. Data can be statistically analyzed if desired; an analysis of variance is performed, followed by a Newman-Keuls test for significant differences between pairs of test materials.

Referring to FIG. 3, the $C_8$ AGS is clearly milder than the Standard AGS at four concentrations, i.e., about 0.04%; 0.08%; 0.5%; and 1%. As shown in FIG. 3, $C_8$ AGS has a Patch Test Value of less than 0.6 at concentrations up to about 1%; less than 0.5 at concentrations up to about 0.8%; less than 0.5 at concentrations up to about 0.5%; and less than 0.3 at concentrations up to about 0.2%.

Example 21

A preferred facial cleanser formula using a $C_8$ AGS similar to that of Example 1 is set out in Table 8. It has a milder surfactant system than one made with a comparable amount of Standard AGS.

TABLE 8

| Ingredient | Solution % |
| --- | --- |
| Sodium $C_8$ AGS | 5 |
| Lauramide DEA | 5 |

TABLE 8-continued

| Ingredient | Solution % |
| --- | --- |
| Cocoamidopropyl Betaine | 2.5 |
| Sodium n-Lauroyl Sarcosinate | 2.5 |
| Dowicil 200 (quaternium-15) | 0.2 |
| Perfume | 0.05 |
| Water | 84.75 |
| Total | 100.00% |

Lauramide DEA, the betaine, and the sarcosinate are foam enhancers and are present at relative levels of 33⅓%, 16⅔%, and 16⅔%, respectively, by weight of the total surfactant system. The foam stability for this liquid composition is much better than one in which the foam enhancers are replaced with $C_8$ AGS.

Example 22

Steps 1 and 2 are similar to Example 1. Step 3 is similar to Example 1, except that under sulfonation provides a higher foaming $C_8$ AGS product.

Under sulfonation in this Example uses 9.11 parts of the alkyl glycidyl ether of Step 2; 17.75 parts of water; 351 parts of sodium meta-bisulfate; and 0.38 part of sodium hydroxide. A heel of $C_8$ AGS from earlier production, about 10% of the total reaction mass, is added to the starting reagents. Sodium ethylenediaminetetraacetate (EDTA) is added as a processing aid to chelate metals such as iron. The mixture is well stirred and heated until it reaches a temperature of about 360° F. (182° C.) (exothermic heat of reaction will supply part of the heating). The reaction mix is held at 360° F. (182° C.) for about 10–25 minutes and then cooled to room temperature. The pH is adjusted to about 9 with sodium hydroxide. This product is about 70% $C_8$ AGS and about 30% unsulfonated materials. The principal components of the unsulfonated materials are propane-1,2-diol alkyl ether and diglyceryl alkyl ether, described hereinabove as acetone soluble. The alkyl groups correspond to the starting materials. Under sulfonation can produce 5–50% unsulfonated materials, preferably 10–40%. The under sulfonated $C_8$ AGS is a better foamer than the fully sulfonated $C_8$ AGS.

What is claimed is:

1. An ultra mild skin cleansing composition comprising:
   a) from 10% to 80% by weight of said composition of an ultra mild, good foaming surfactant consisting essentially of an alkyl glyceryl ether sulfonate surfactant having a hydrophobic group which contains an alkyl chain of 8 carbon atoms; and wherein said alkyl glyceryl ether sulfonate surfactant has a Relative Skin Barrier Destructive Value of from about 0.1 to about 0.9;
   b) from 10% to 40% by weight of said composition of a moisturizer;
   c) from 0.1% to 5% by weight of said composition of a polymeric skin feel aid; and
   d) from 5% to 25% by weight of said composition of soap.

2. An ultra mild skin cleansing composition according to claim 1 which further comprises from 5% to 30% by weight of a foam enhancer based on the weight of surfactant in the composition.

3. An ultra mild skin cleansing composition according to claim 2 wherein the foam enhancer is selected from the group consisting of alkyl polyglycoside detergents, amine oxide detergents, fatty acid alkanolamides, betaines, water-soluble halide salts, and $C_8$ alkyl glyceryl ether sulfonate acetone solubles.

4. An ultra mild skin cleansing composition according to claim 3 which comprises from 20% to 50% by weight of said composition of an ultra mild, good foaming surfactant consisting essentially of an alkyl glyceryl ether sulfonate surfactant having a hydrophobic group which contains an alkyl chain of 8 carbon atoms; and wherein said alkyl glyceryl ether sulfonate surfactant has a Relative Skin Barrier Destructive Value of from about 0.1 to about 0.9.

5. An ultra mild skin cleansing composition according to claim 4 wherein said alkyl glyceryl ether sulfonate surfactant has a Relative Skin Barrier Destructive Value of from about 0.1 to about 0.5.

6. An ultra mild skin cleansing composition according to claim 5 wherein the weight ratio of said alkyl glyceryl ether sulfonate surfactant to soap ranges from 2:1 to 12:1.

* * * * *